United States Patent
Miwa et al.

(10) Patent No.: US 10,603,304 B1
(45) Date of Patent: Mar. 31, 2020

(54) COMPOSITIONS AND METHODS FOR TREATING ANXIETY

(71) Applicant: Julie M. Miwa, Hellertown, PA (US)

(72) Inventors: Julie M. Miwa, Hellertown, PA (US);
Huaixing Wang, Horsham, PA (US);
Kristin R. Anderson, Middlesex, NJ (US)

(73) Assignee: Julie M. Miwa, Hellertown, PA (US)

( * ) Notice: Subject to any disclaimer, the term of this patent is extended or adjusted under 35 U.S.C. 154(b) by 90 days.

(21) Appl. No.: 15/287,732

(22) Filed: Oct. 6, 2016

Related U.S. Application Data

(60) Provisional application No. 62/237,969, filed on Oct. 6, 2015.

(51) Int. Cl.
*A61K 31/403* (2006.01)
*A61K 31/13* (2006.01)

(52) U.S. Cl.
CPC ............ *A61K 31/403* (2013.01); *A61K 31/13* (2013.01)

(58) Field of Classification Search
CPC .............................. A61K 31/403; A61K 31/13
See application file for complete search history.

(56) References Cited

U.S. PATENT DOCUMENTS 9,180,191 B2 * 11/2015 Sheehan .............. A61K 31/407

OTHER PUBLICATIONS

Tucci et al., Do different mechanisms underlie to anxiogenic effects of systemic nicotine?, 2003, Behavioural Pharmacology, 14(4), pp. 323-329, Abstract Only.*
Tekinay et al., A role for LYNX2 in anxiety-related behavior, 2009, PNAS, vol. 106, No. 11, pp. 4477-4482.*

* cited by examiner

*Primary Examiner* — Rachael E Bredefeld
*Assistant Examiner* — Chris E Simmons
(74) *Attorney, Agent, or Firm* — Lewis Roca Rothgerber Christie LLP

(57) ABSTRACT

A method of treating anxiety in a subject having a mutation in the lynx2 gene and suffering from anxiety, includes administering to the subject an effective amount of a nicotinic blocker and/or an effective amount of a selective antagonist of the nicotinic acetylcholine receptor alpha-7 (nAChR α7) subunit.

6 Claims, 20 Drawing Sheets
(12 of 20 Drawing Sheet(s) Filed in Color)
Specification includes a Sequence Listing.

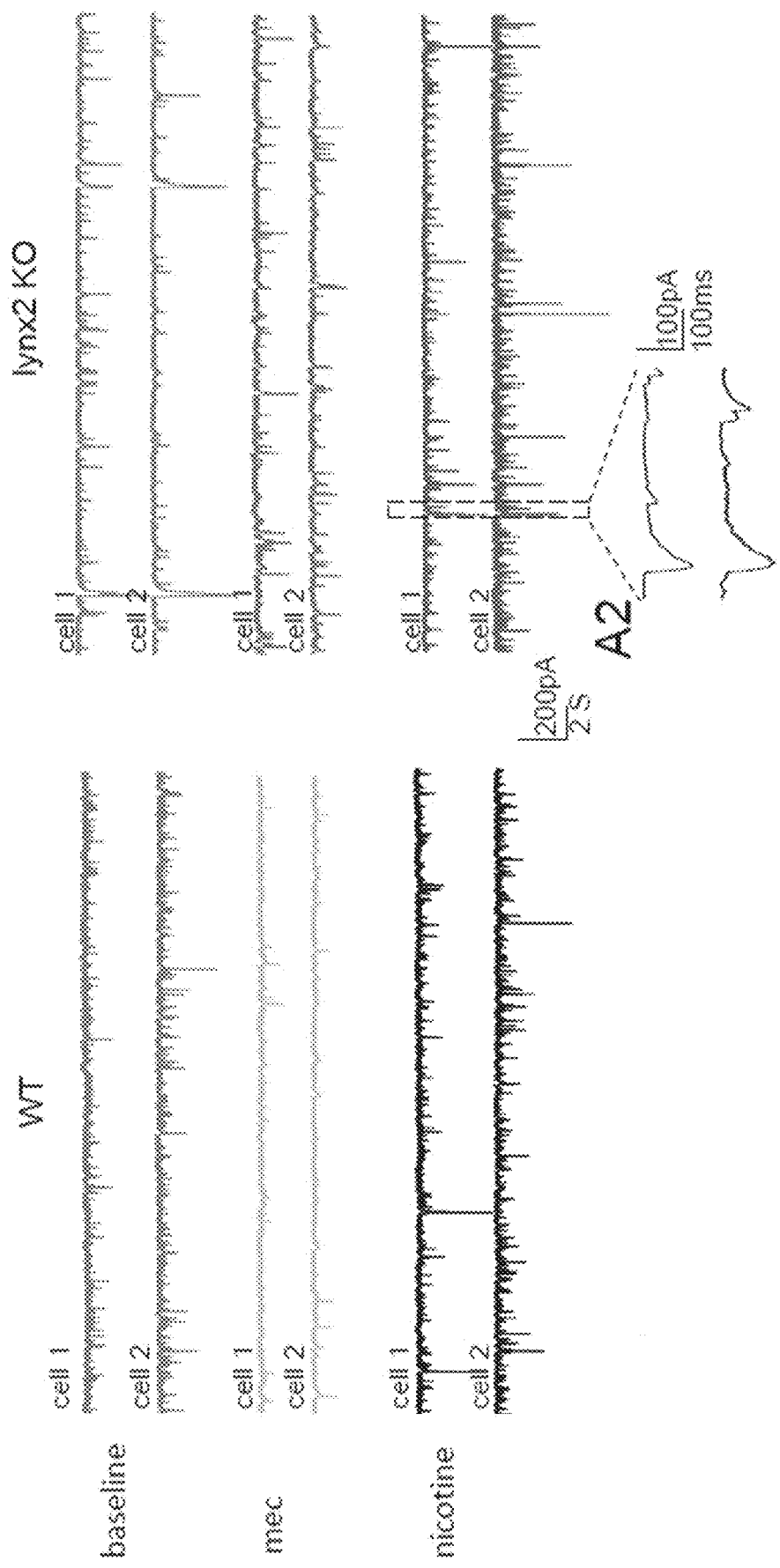

Wild-type lynx2 model

COMPOSITIONS AND METHODS FOR TREATING ANXIETY

CROSS-REFERENCE TO RELATED APPLICATION(S)

The present application claims priority to and the benefit of U.S. Provisional Application Ser. No. 62/237,969 filed on Oct. 6, 2015, entitled "Anxiety Regulation Through Lynx2-mediated Cholinergic Modulation," the entire content of which is incorporated herein by reference.

INCORPORATION BY REFERENCE

The instant application contains a Sequence Listing which has been submitted electronically in ASCII format and is hereby incorporated by reference in its entirety. Said ASCII copy, created on Dec. 15, 2016, is named 129621 SEQLISTING.txt and is 9,896 bytes in size.

BACKGROUND

Anxiety is a natural reaction to stress that quickly heightens awareness for an individual during a dangerous situation, which has a potential survival benefit. Many individuals are able to reduce or extinguish the anxiety after the danger is over and return to a normal baseline state. Individuals with excessive anxiety may have difficulty controlling their anxiety, and this can have a deleterious effect on their quality of life. People with anxiety disorders can have an amplification of the anxiety response every time they experience the trigger or an approximation of the trigger. Of the main types of anxiety disorders—social anxiety disorders, panic disorders, phobias, and generalized anxiety disorder—generalized anxiety lacks a specific cause while the other disorders have a purported if not known cause. Treating these anxiety disorders can be difficult because each type requires different treatments and therapeutic approaches. Additionally, fear and anxiety are tied with a strong memory network. In order to treat these disorders, reintroduction of a neutral quality to stimuli that may have become associated with trauma is typically required.

Many previous studies have implicated the amygdala as the brain structure involved in many anxiety phenotypes, in both human and mouse models and as a mediator of the emotional output of fear and anxiety. Hyperexcitability and hyperactivity are key features of anxiety disorders. Inputs from many brain regions converge on the amygdala to allow an individual to judge the true danger of a situation and create the proper response. Significant links between the amygdala and fear-based memory could explain why traumatic events may appear to be encoded for a longer period than might be adaptive or helpful to the individual. Manipulating the emotional charge to traumatizing stimuli could potentially alter the inappropriate response.

Current prescribed medications deliver an instant, but not long lasting, relief of anxiety through their sedative, anxiolytic, and relaxant properties. There is evidence that anxious patients may try to self-medicate through the intake of nicotine, although differential responsiveness to the effects of nicotine may blunt this effect. A specific nicotinic acetylcholine receptor subtype (nAChRs), $\alpha 7$, has been implicated in regulating the network excitability of the amygdala. Cholinergic modulation, therefore, is a factor for the investigation of anxiolytic strategies. The cholinergic system plays a role in many facets of brain function, including learning and memory and plasticity. A consideration of long-term effects of cholinergic modulation, including plasticity mechanisms, may be informative to our understanding of anxiety mechanisms.

SUMMARY

In some embodiments of the present invention, a method of treating anxiety in a subject having a lynx2 mutation includes administering to the subject an effective amount of a nicotinic blocker selected from the mecamylamine, quirestine, hexamethonium bromide, tempoxime hydrochloride, buproprion, amantidine, memantine, enantiomers thereof, or combinations thereof; and/or an effective amount of a selective antagonist of the nicotinic acetylcholine receptor alpha-7 (nAChR $\alpha 7$) subunit selected from methyllycaconitine (MLA), condelphine, aconitane, talatisamine, bullatineB, delphamine, bikhaconitine, pyrodelphonine, winklerlin, delelatine, analogs, enantiomers, and isomers thereof, lynx1 protein, lynx2 protein, an elapid snake venom toxin protein, a marine snail toxin protein, clozapine, COG133 peptide, orcombinations thereof.

In some embodiments of the present invention, a kit for identifying a lynx2 mutation in a subject or a kit for determining the presence of a lynx2 mutation in a subject suffering from anxiety includes a first oligonucleotide primer having a sequence selected from SEQ ID NO:11 or 12 for amplifying a lynx2 gene sequence from the subject. In some embodiments, the kit also includes a second oligonucleotide primer having a sequence selected form SEQ ID NO: 11 or 12. In some embodiments, the kit also includes a therapeutic molecule for treating lynx2-dependent anxiety, the therapeutic molecule including a nicotinic blocker selected from mecamylamine, quirestine, hexamethonium bromide, tempoxime hydrochloride, buproprion, amantidine, memantine, enantiomers thereof, or combinations thereof; and/or a selective antagonist of the nicotinic acetylcholine receptor alpha-7 (nAChR $\alpha 7$) subunit selected from methyllycaconitine (MLA), condelphine, aconitane, talatisamine, bullatineB, delphamine, bikhaconitine, pyrodelphonine, winklerlin, delelatine, analogs, enantiomers, and isomers thereof, lynx1 protein, lynx2 protein, an elapid snake venom toxin protein, a marine snail toxin protein, clozapine, COG133 peptide, or combinations thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3A shows sample electrode traces of spontaneous inhibitory post-synaptic currents (sIPSCs) in two simultaneously recorded pyramidal neurons in wild type (WT) and lynx2KO mice in the presence of an artificial cerebrospinal fluid (ASCF) alone (baseline), ASCF with 20 uM mecamylamine (mec), or ASCF with 10 uM nicotine, in which according to embodiments of the present invention.

DETAILED DESCRIPTION

A gene, lynx2, is expressed and highly enriched in the amygdala. When lynx2 is removed from a mouse model, these mice show heightened anxiety and are aberrant in social interactions. While not bound by any particular theory, the present disclosure contemplates that lynx2 alters the cellular behavior in the basolateral amygdala (BLA), a subset of the amygdala, and that this alteration can lead to the behavioral output of lessened anxiety. Additionally, the present disclosure contemplates that when lynx2 is expressed, its protein binds to nicotinic acetylcholine receptors (nAChR) and dampens the response to acetylcholine.

Figure 1:
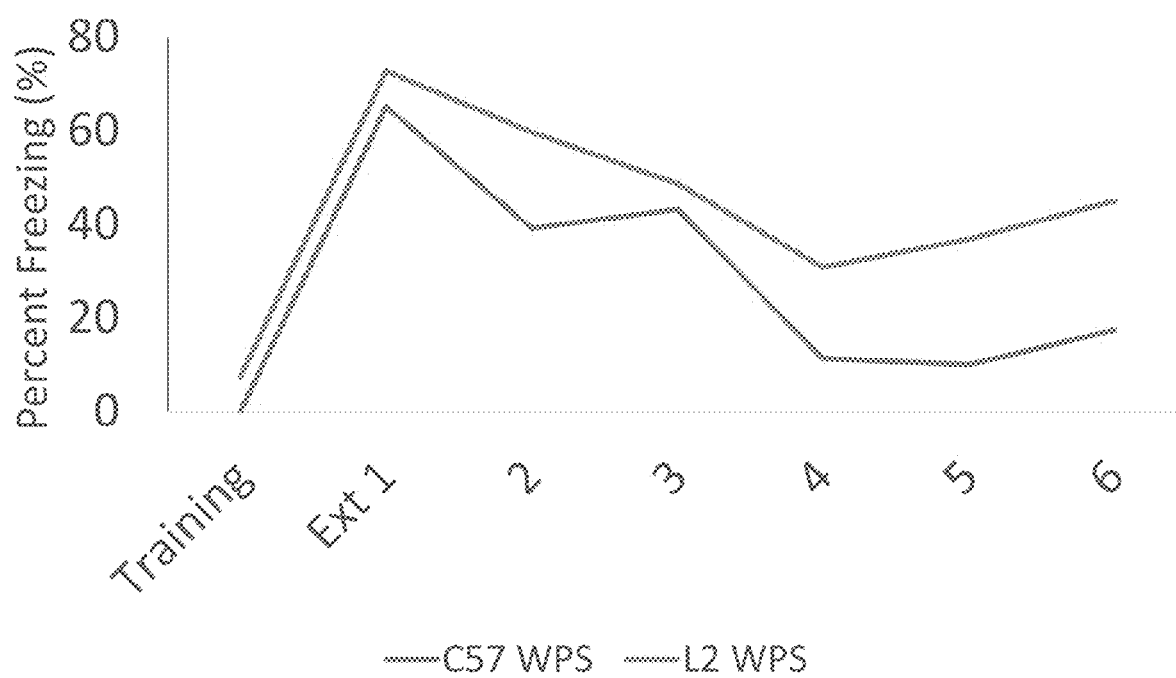
FIG. 1 is a graph of the amount of freezing observed in wild type mice (C57 WPS) (blue line) and lynx2 knock out mice (L2 WPS) (red line) after fear training followed by a change in the training to measure fear extinction, according to embodiments of the present invention.
Figure 2A:
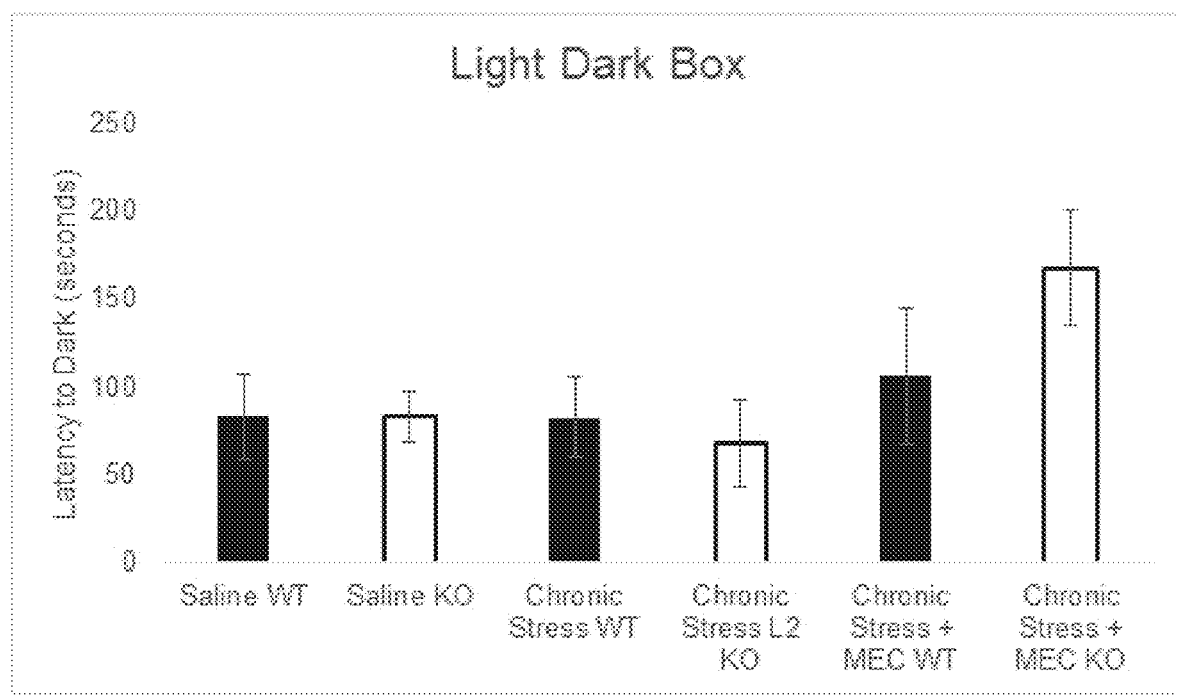
FIG. 2A is a graph of the time in seconds (latency) for wild type (WT) (black bars) or lynx2 knock out (KO) (white bars) mice to enter a dark enclosed environment under conditions of saline, chronic stress, or chronic stress with administration of mecamylamine (mec) as indicated, according to embodiments of the present invention.
Figure 2B:
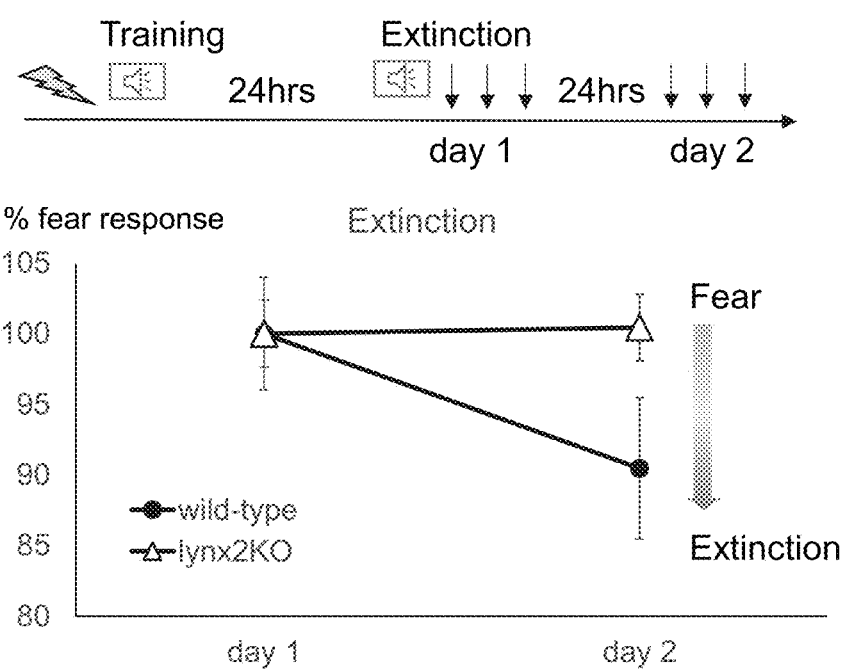
FIG. 2B is a graph of fear observed in wild type (black circles) and lynx2KO mice (white triangles) after fear training (an electric shock depicted in yellow) associated with a noise for 24 hours followed by the same noise without the shock to measure the mouse's capability to lose the fear, according to embodiments of the present invention.
Figure 2C:
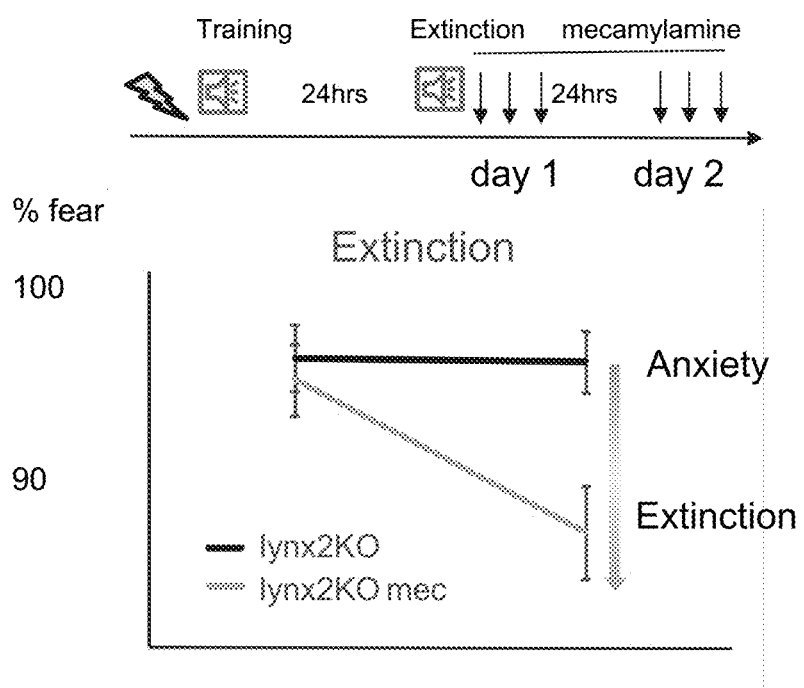
FIG. 2C is a graph of fear observed in lynx2KO mice during the fear extinction experiment of FIG. 2B with a group of lynx2KO mice receiving mecamylamine (mec), according to embodiments of the present invention.

Embodiments of the present invention are based on the contemplation that mice lacking the lynx2 gene (lynx2 knock out (KO)mice have increased anxiety caused by a lack of synaptic weakening. Because of this increase in the strength of the synapse in lynx2KO mice, these mice retain anxious behavior. Indeed, as shown in FIG. 1, lynx2KO mice are slow to unlearn a previous anxiety-inducing activity. However, as shown in FIGS. 2A-2C, the lynx2KO mice are able to be alleviated of the retained stress and anxiety with the nicotinic receptor blocker, mecamylamine (mec). In a light dark box experiment (FIG. 2A), lynx2KO mice were observed to have increased latency to dark with administration of mec as opposed to lynx2KO mice without mec. Similarly, in fear extinction experiments (FIGS. 2B-2C) lynx2KO mice showed an increased ability to unlearn a fear associated with a noise with administration of mec compared to lynx2KO mice without mec.

Figure 3C:
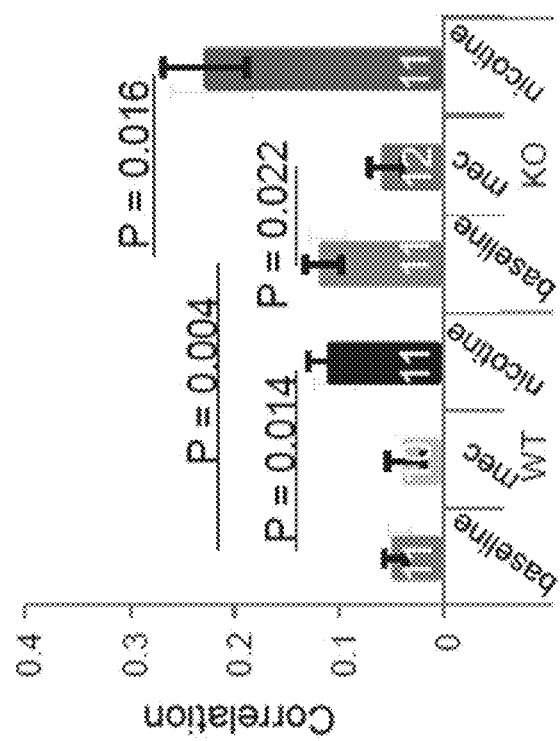
FIG. 3C is a graph summarizing peak correlation of sIPSCs for the mice and conditions in FIG. 3A, according to embodiments of the present invention.
Figure 3B:
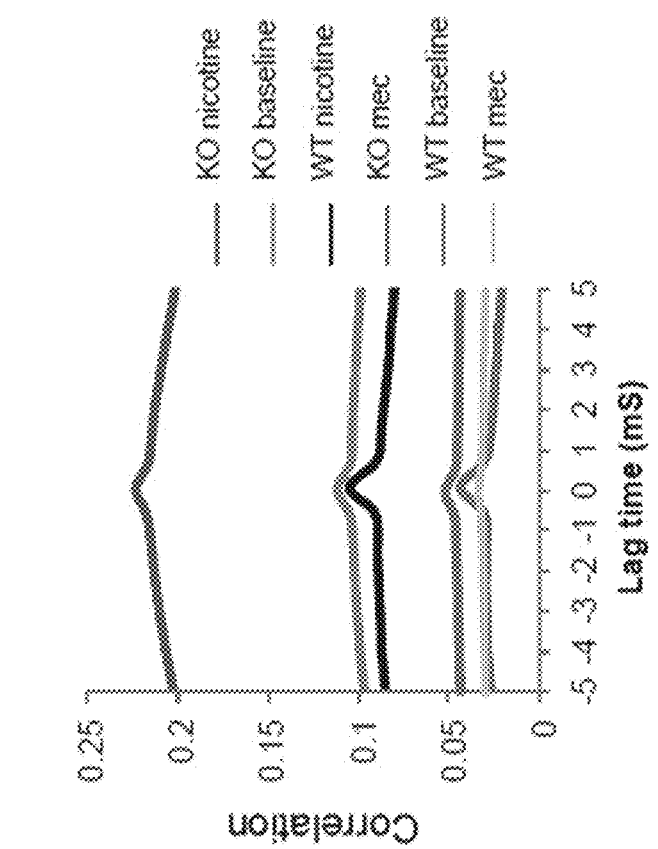
FIG. 3B is a graph of cross-correlation analysis of sIPSCs in the double-record neurons for the mice and conditions of FIG. 3A where KO nicotine is shown in red, KO baseline is shown in blue, WT nicotine is shown in black, KO mec is shown in green, WT baseline is shown in grey, and WT mec is shown in yellow, according to embodiments of the present invention.
Figure 4A:
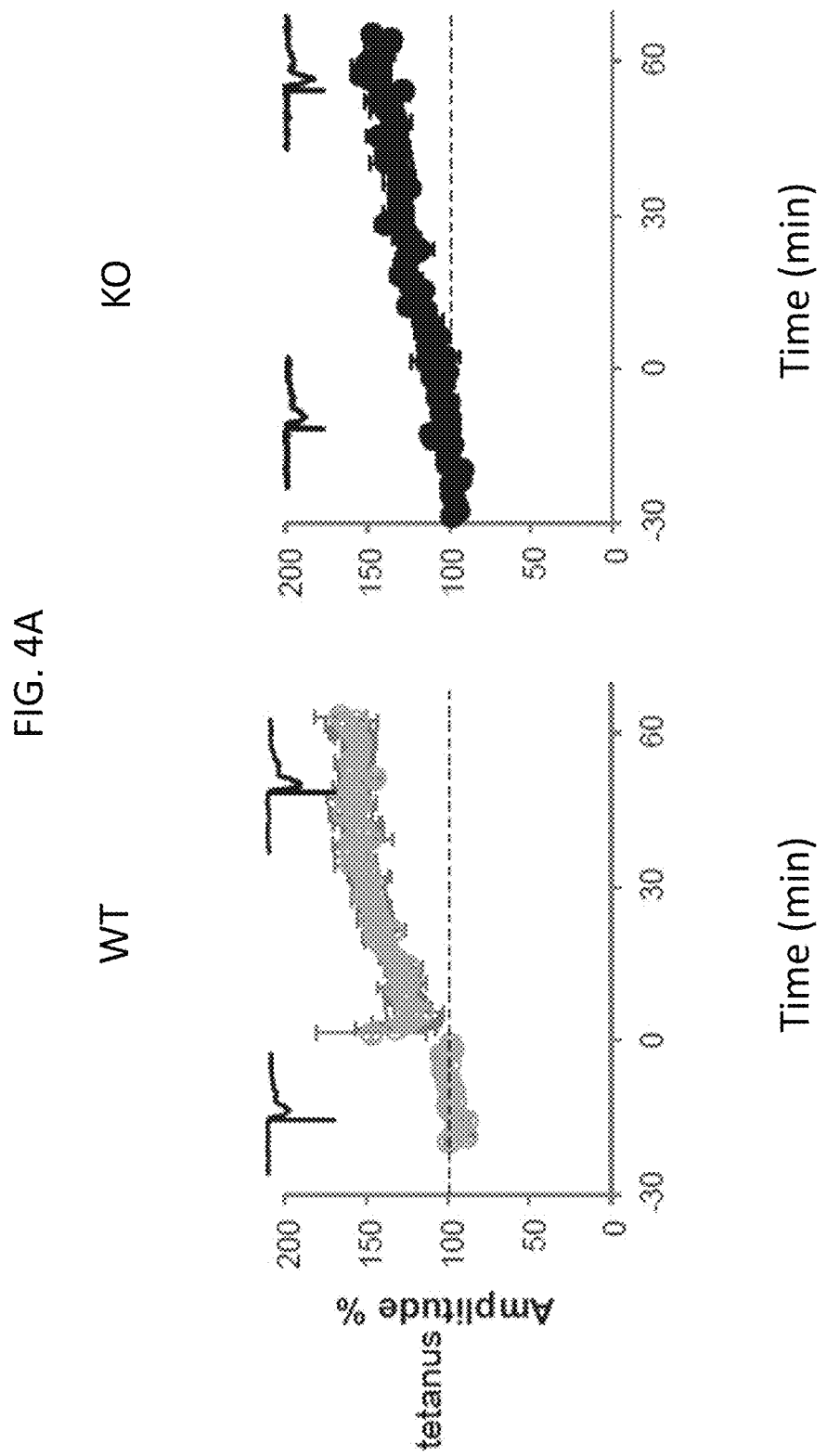
FIG. 4A shows graphs of stimulating electrode traces from long term potentiation (LTP) experiments using extracellular recordings for evoked field excitatory post-synaptic potentials (fEPSPs) in entorhinal cortices (EC) brain slices in ACSF solution from both wild type (WT) and lynx2 knockout (KO) mice before (left of zero minutes) and after (right of zero minutes) tetanus, according to embodiments of the present invention.
Figure 4B:
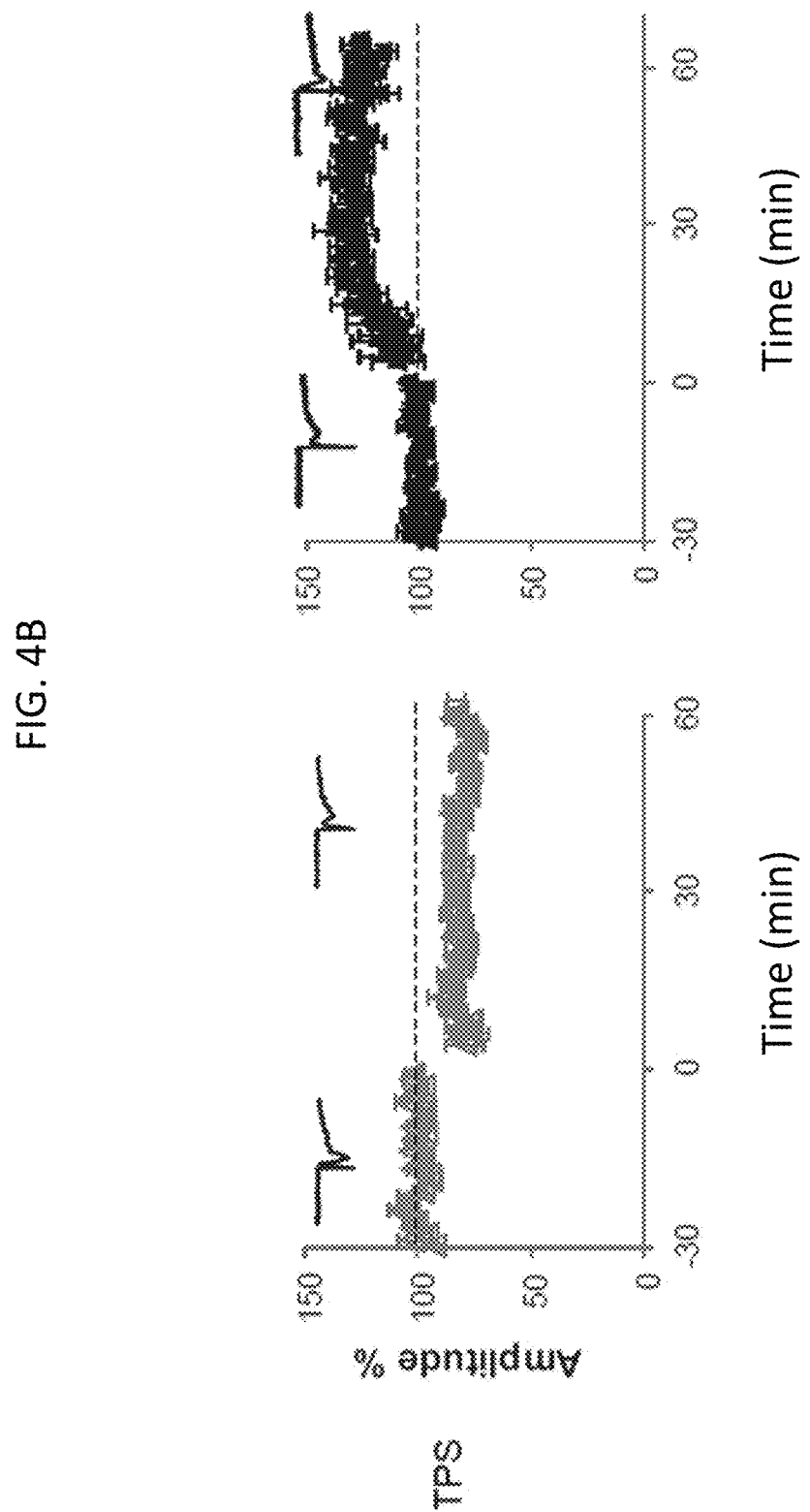
FIG. 4B shows graphs of stimulating electrode traces from long term depression (LTD) experiments using extracellular recordings for evoked field excitatory post-synaptic potentials (fEPSPs) in entorhinal cortex (EC) brain slices in ACSF solution from both wild type (WT) and lynx2 knockout (KO) mice before (left of zero minutes) and after (right of zero minutes) theta pulse stimulations (TSP), according to embodiments of the present invention.
Figure 4C:
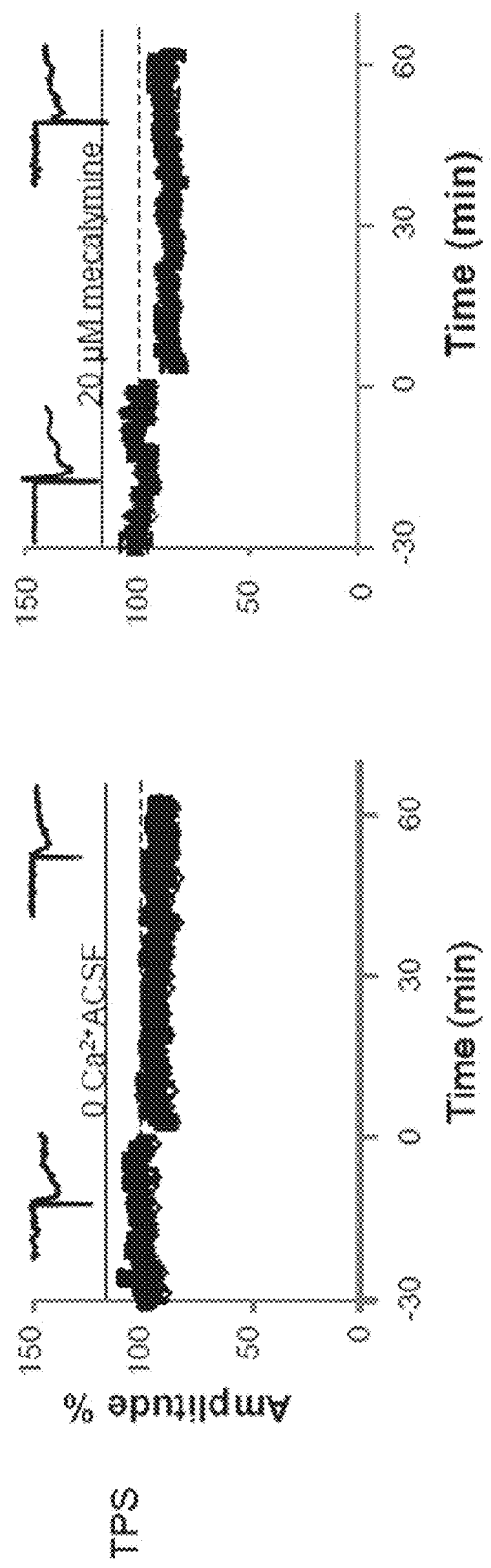
FIG. 4C shows graphs of stimulating electrode traces from long term depression (LTD) experiments using extracellular recordings for evoked field excitatory post-synaptic potentials (fEPSPs) in entorhinal cortex (EC) brain slices in ACSF solution without Ca2+(0 Ca2+ ACSF) from wild type (WT) and in ACSF solution with 20 mM mecamylamine from lynx2 knockout (KO) mice before (left of zero minutes) and after (right of zero minutes) theta pulse stimulations (TSP), according to embodiments of the present invention.
Figure 4D:
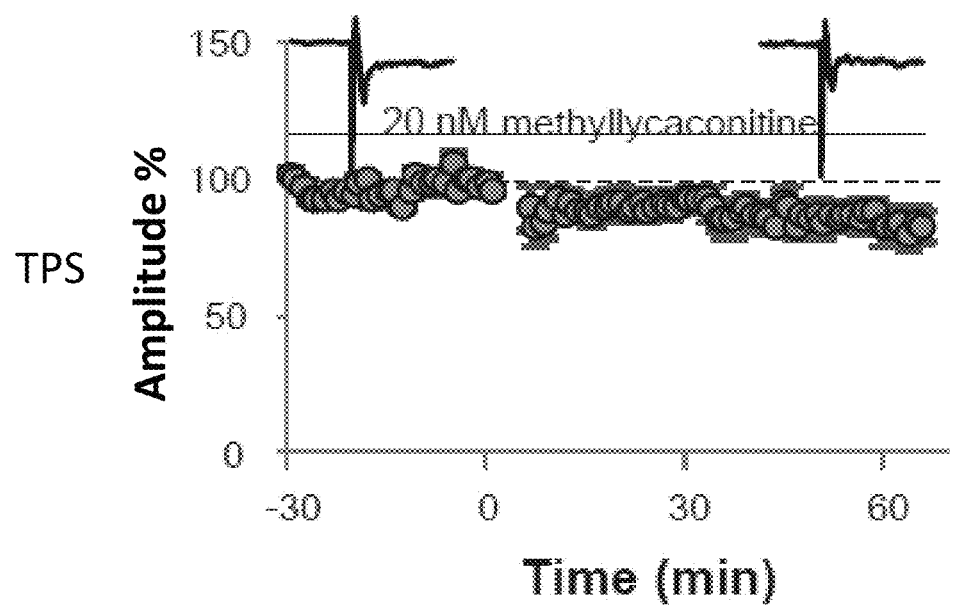
FIG. 4D is a graph of stimulating electrode traces from long term depression (LTD) experiments using extracellular recordings for evoked field excitatory post-synaptic potentials (fEPSPs) in entorhinal cortex (EC) brain slices in ACSF solution with 20 mM methyllycaconitine (MLA) from lynx2 knockout (KO) mice before (left of zero minutes) and after (right of zero minutes) theta pulse stimulations (TSP), according to embodiments of the present invention.
Figure 4F:
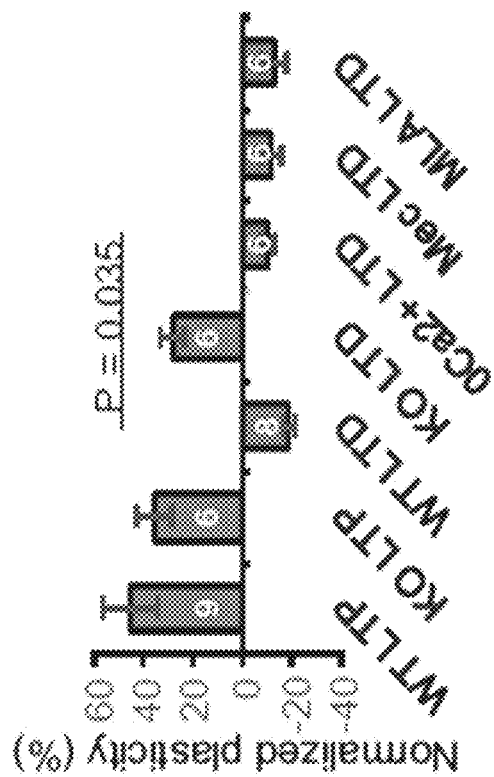
FIG. 4F is a graph summarizing the mean normalized plasticity (percent (%) change) of the LTP and LTD experiments of FIGS. 4A-4D, according to embodiments of the present invention.
Figure 4E:
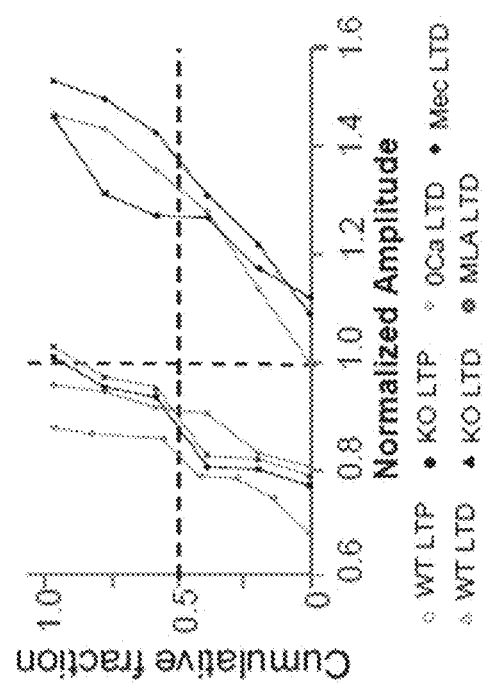
FIG. 4E is a graph of the cumulative histogram of plasticity of the LTP and LTD experiments of FIGS. 4A-4D as indicated, according to embodiments of the present invention.

Rescue of the lynx2KO phenotype was also observed physiologically in electrode traces of spontaneous inhibitory post-synaptic currents (sIPSCs) in pyramidal neurons of wild type (WT) and lynx2KO mice as shown in FIGS. 3A-3C. In field excitatory post-synaptic potentials (fEPSPs) in entorhinal cortice (EC) brain slices from WT and lynx2KO mice as shown in FIGS. 4A-4D, the anxiety phenotype of lynx2KO mice was shown to be specific to the nAChR alpha 7 subunit. As shown in FIG. 4D, the selective alpha7 (α 7) nAChR antagonist, methyllycaconitine (MLA) was able to rescue induced long term depression (LTD) in the amygdala (EC) neurons of lynx2KO mice.

Figure 5A:
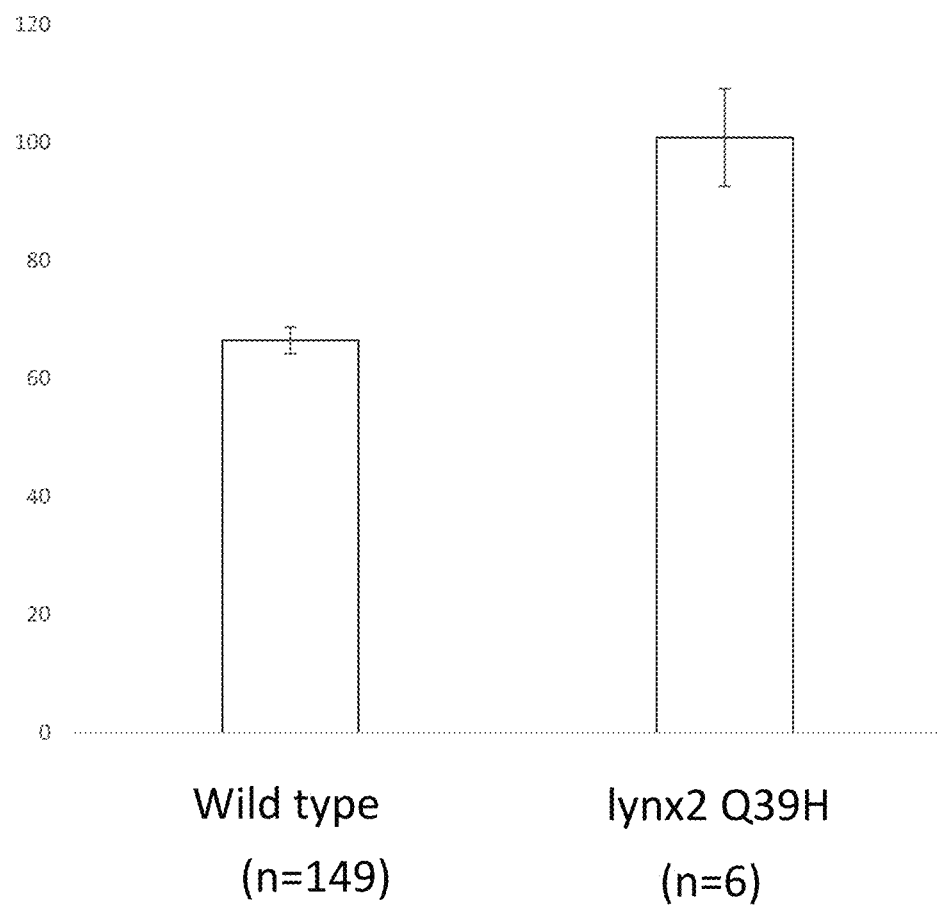
FIG. 5A is a graph showing the average anxiety scores obtained using a Fisher's exact test in human subjects with a wild type (normal) lynx2 gene (left) and human subjects with a mutant lynx2 gene (lynx2Q39H), the sample size (n) was 149 for the wild type group and 6 for the lynxQ39H group, according to embodiments of the present invention.
Figure 5B:
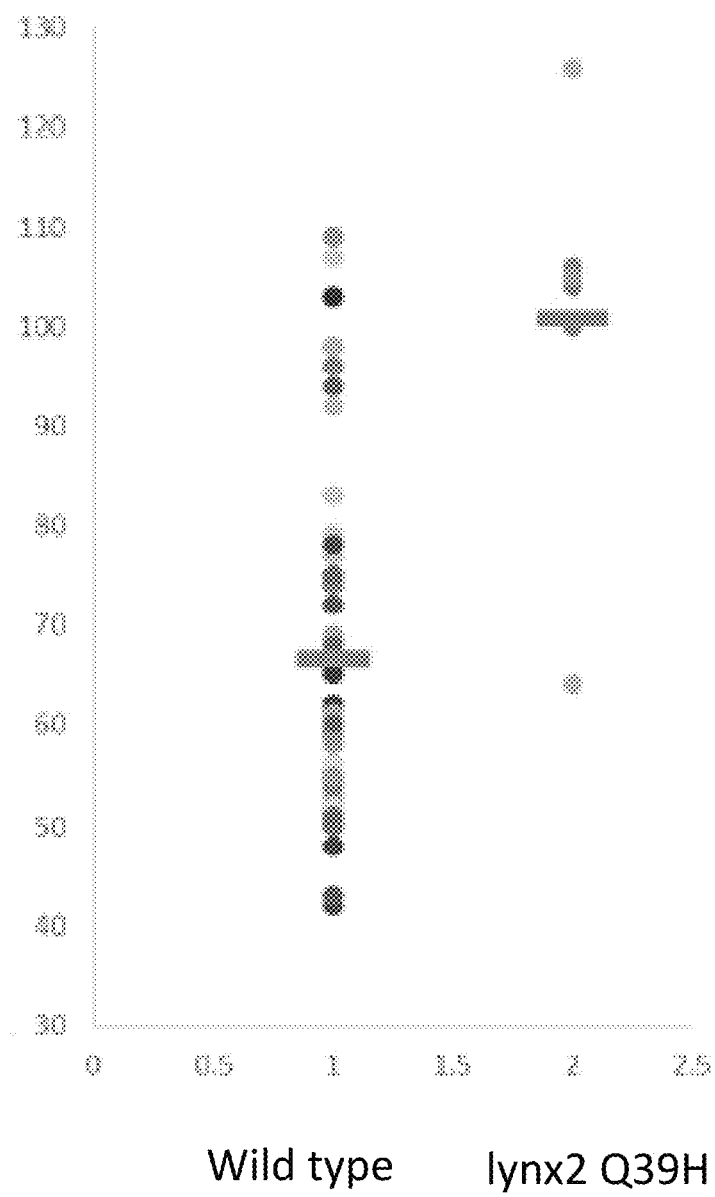
FIG. 5B depicts individual anxiety scores from the human subjects of FIG. 5A, in which each differently colored dot represents a different person and their anxiety score; the horizontal blue bar represents the mean anxiety value, according to embodiments of the present invention.
Figure 6:
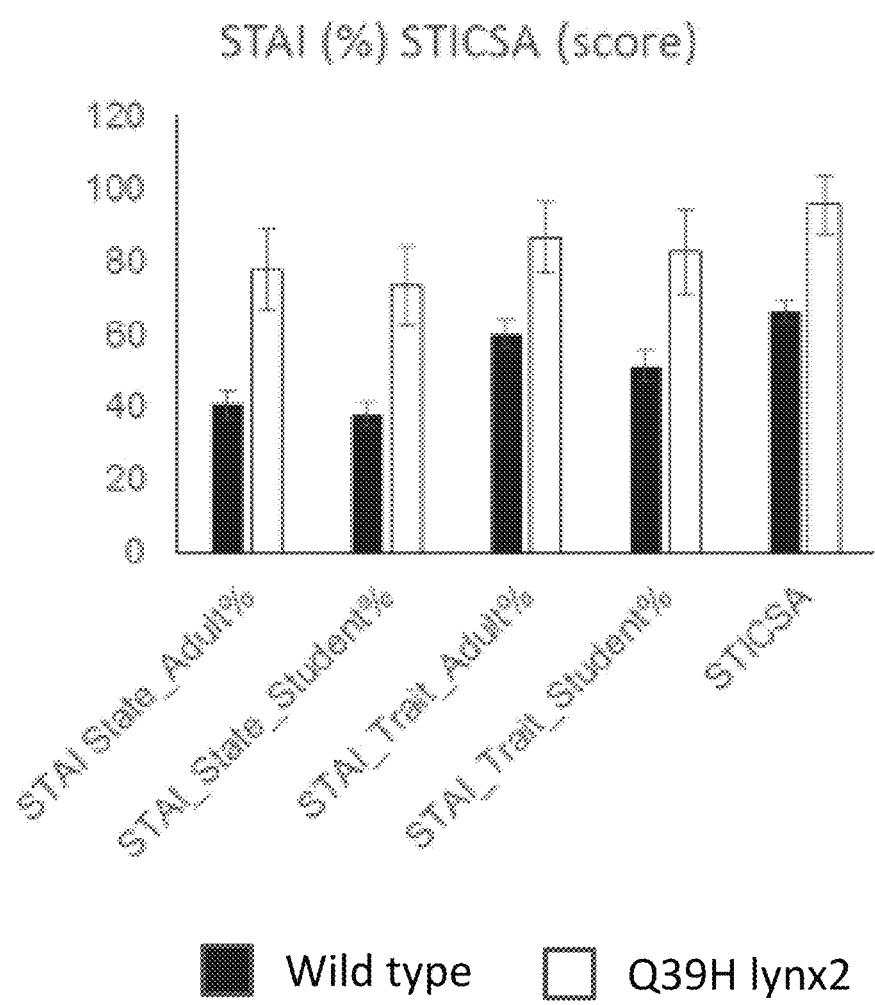
FIG. 6 is a graph showing the results of two anxiety tests, the State-Trait Anxiety Inventory (STAI) and the State-Trait Inventory for Cognitive and Somatic Anxiety (STICSA), as indicated, in human subjects (adult and students) with a wild type lynx2 gene (black bars) and human subjects with a mutant lynx2 gene (lynx2Q39H)(white bars), according to embodiments of the present invention.

Based on the observations that lynx2KO mice have increased anxiety and this anxiety is alleviated or decreased with the nicotinic receptor blocker, mecamylamine (mec), and the α 7 nAChR antagonist, methyllycaconitine (MLA), human's suffering from anxiety were observed. As shown in FIGS. 5A-5B, human subjects were analyzed using the Fisher's exact anxiety test in which subjects having a wild type lynx2 gene had a lower anxiety score and subjects having a Q39H mutation in the lynx2 gene had higher anxiety scores. Additionally subjects having the lynx2Q39H mutation also had higher anxiety scores for both the State-Trait Anxiety Inventory (STAI) and the State-Trait Inventory for Cognitive and Somatic Anxiety (STICSA), as shown in FIG. 6.

Based on these observations in mice and human subjects, embodiments of the present invention contemplate treating anxiety in a patient having a lynx2 mutation by administering a selective nicotinic receptor blocker and/or an α7 AChR antagonist.

Figure 7A:
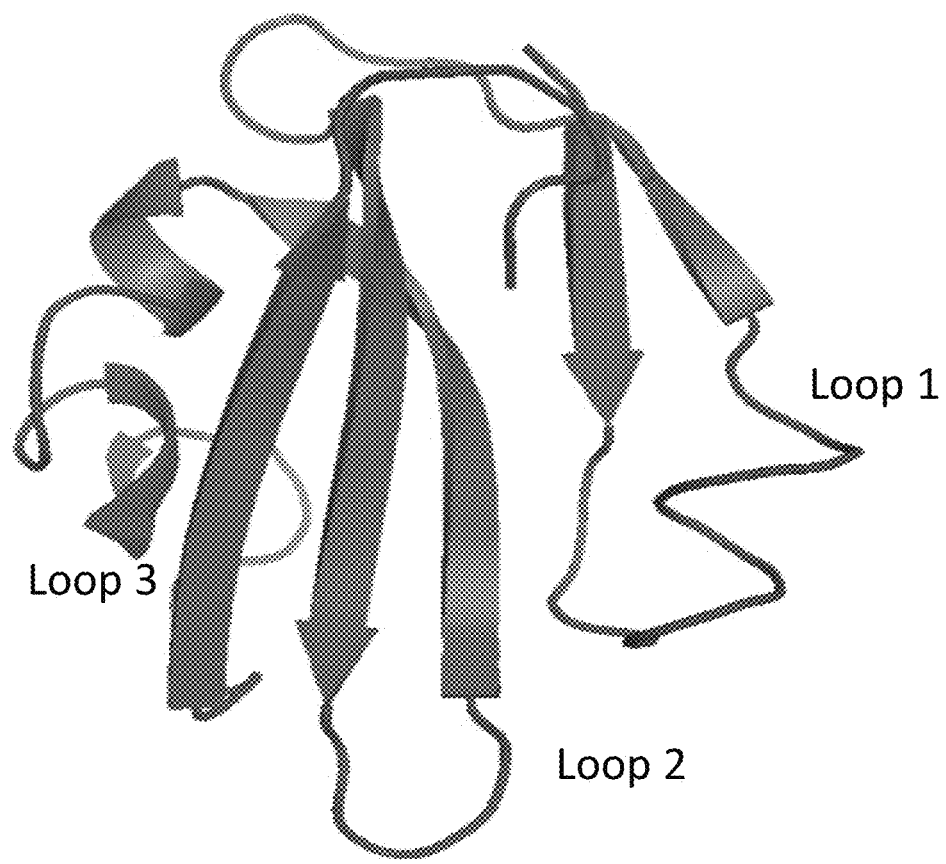
FIG. 7A is a computer protein model of wild type lynx2 protein (shown in red), according to embodiments of the present invention.
Figure 7B:
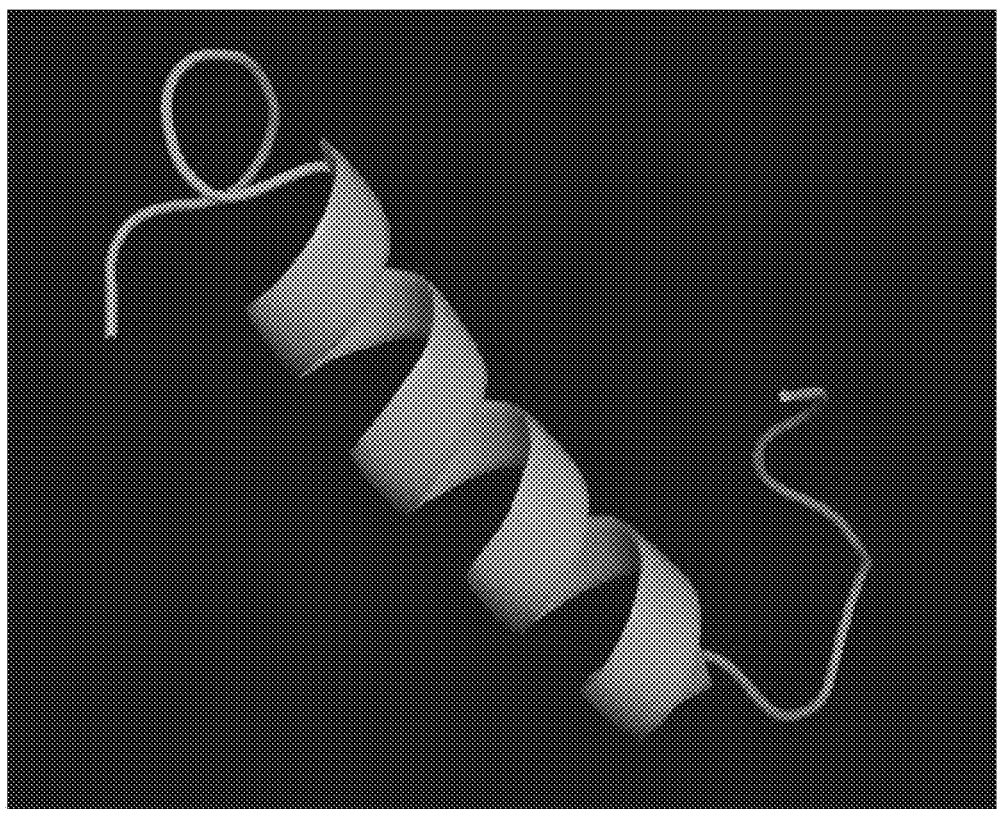
FIG. 7B is a computer protein model of a frameshift mutation sequence at position 1 of lynx2 (SEQ ID NO: 2) (shown in green), according to embodiments of the present invention.
Figure 7C:
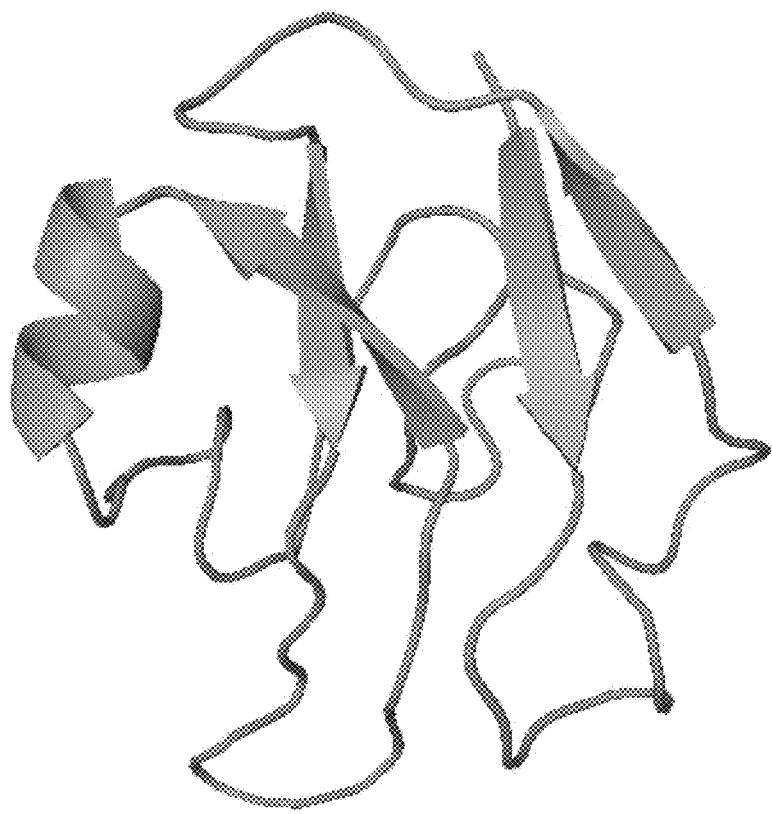
FIG. 7C is a computer protein model of a frameshift mutation resulting in a premature stop of lynx 2 (SEQ ID NO: 3) (shown in green), according to embodiments of the present invention.
Figure 7D:
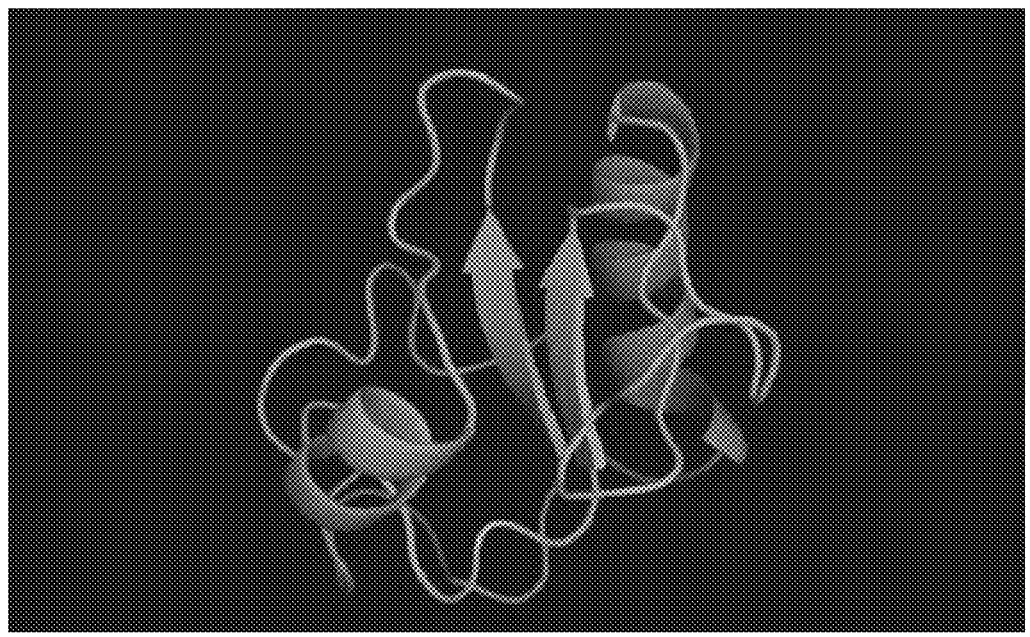
FIG. 7D is a computer protein model of a frameshift mutation resulting in a premature stop of lynx 2 (SEQ ID NO: 4) (shown in green), according to embodiments of the present invention.
Figure 7E:
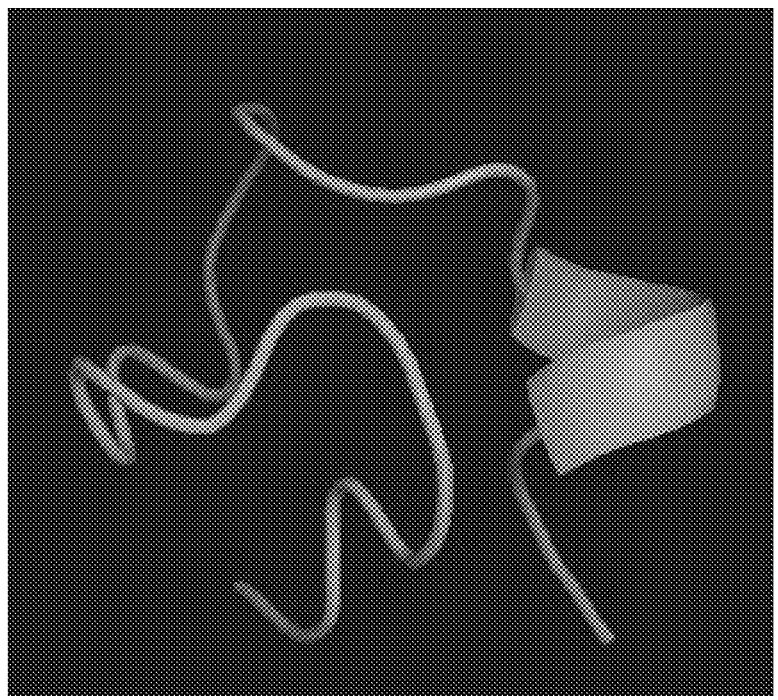
FIG. 7E is a computer protein model of a frameshift mutation resulting in a premature stop of lynx 2 (SEQ ID NO: 5) (shown in green), according to embodiments of the present invention.
Figure 7F:
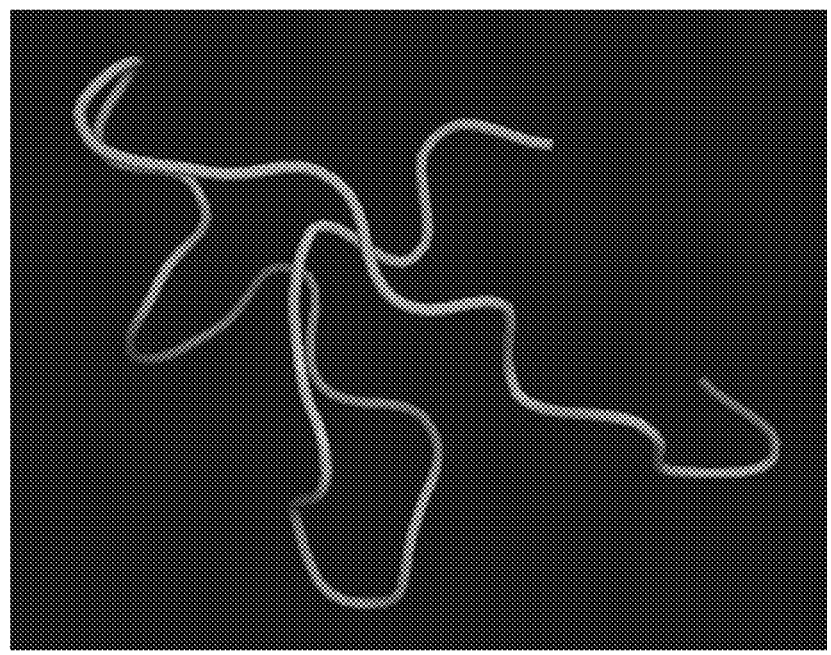
FIG. 7F is a computer protein model of a stop-gain mutation of lynx 2 (SEQ ID NO: 6) (shown in green), according to embodiments of the present invention.

In some embodiments of the present invention, the lynx2 mutation conferring an anxiety phenotype includes any deletion or mutation that abolishes or decreases the wild type function of the lynx2 protein as shown in the protein modeling of FIGS. 7A-7F. For example, the lynx2 mutation may include a null deletion, a frameshift mutation, a nonsense mutation (e.g., a stop or stop-gain mutation) and/or a point mutation in the lynx2 gene. Protein modeling of a WT lynx2 (SEQ ID NO: 1) sequence is shown in FIG. 7A, for a frameshift mutation sequence at position 1: VGPRHRGNFLRIVLASRLCAANPVLPV*RIPAEQRLL-LPRVHCELHGERSRHVSERSDGA KCRDHVPQVLCI-ISGLSHRLCRVPVLLLPRETELSLHQLLQHPSL (SEQ ID NO: 2) is modeled in FIG. 7B, frameshift mutation sequences resulting in premature stops are modeled in FIGS. 7C, 7D, and 7E for sequences IQCYQCEEFQLNNDC-SSPEFIVNCTVNVQDMCQKEVMEQSAGIMYRILCIIS-GLSHRLCR VPVLLLPRETELSLHQLLQHPSL (SEQ ID NO: 3), IQCYQCEEFQLNNDCSSPEFIVNCTVNVQD-VSERSDGAKCRDHVPQVLCIISGLSHRLCR VPVLLL-PRETELSLHQLLQHPSL (SEQ ID NO: 4), and IQCYQ-CEEFQLNNDCSSPEFIQ (SEQ ID NO: 5), respectively, and a stop-gain mutation for sequence IQCYQ-CEEFQLNNDCSSPEFIVNCTVNV (SEQ ID NO: 6), is modeled in FIG. 7F.

In some embodiments, the lynx2 mutation includes the loss or substitution of glutamine (Q) at position 39 of the mature lynx2 protein (amino acid) sequence as underlined: IQCYQCEEFQLNNDCSSPEFIVNCTVNVQDMCQKEV-MEQSAGIMYRKSCASSAACLIAS AGYQSFCSPG-KLNSVCISCCNTPLCN (SEQ ID NO: 1). In some embodiments, the lynx2 mutation in a subject suffering from anxiety includes any amino acid substitution of the glutamine at position 39. In some embodiments, the lynx2 mutation in a subject suffering from anxiety includes an amino acid substitution of histidine (H) at position 39. In some embodiments of the present invention, a method of treating anxiety or decreasing anxiety in a subject having a lynx2 mutation includes administering an effective amount of a nicotinic receptor blocker or an α7 AChR antagonist to the subject suffering from a lynx2-dependent anxiety.

In some embodiments of the present invention, the nicotinic receptor blocker may include mecamylamine, quirestine, hexamethonium bromide, tempoxime hydrochloride, buproprion, amantidine, memantine, enantiomers thereof, or a combination thereof. The similar structure and function of these nicotinic receptor blockers is described in the art, for example, for mecamulamine: Young et al., *Clin. Ther.*, 2001 23:532-565; for quirestine: G A Buznikov et al., General Pharmacology: The Vascular System, 29(1), 49-53 (1997); for hexamethonium bromide: "Hexamethonium—Compound Summary," http://pubchem.ncbi.nlm.nih.gov/summary/summary.cgi?cid=3604. 2016-10-06; and for tempoxime hydrochloride: "Tempoxime Hydrochloride—Compound Summary" https://pubchem.ncbi.nlm.nih.gov/compound/113266. 2016 Oct. 6, for buproprion: Slemmer J E et al., *J Pharmacol Exp Ther* 2000; 295: 321-327; for amantidine: Matsubayashi et al., *J Pharmacol Exp Ther,* 1997 May; 281(2):834-44; and for memantine: Aracava Y et al., *J Pharmacol Exp Ther.* 312 (3): 1195-205. doi:10.1124/jpet.104.077172. PMID 15522999 the entire contents of all of which are herein incorporated by reference. the entire contents of all of which are herein incorporated by reference.

In some embodiments of the present invention, the selective α7 AChR antagonist may include methyllycaconitine (MLA), and analogs of MLA, including condelphine, aconitane, talatisamine, bullatineB, delphamine, bikhaconitine, pyrodelphonine, winklerlin, delelatine, and analogs, enantiomers, and isomers thereof. The selective α7 AChR antagonist may also include full length lynx1 protein (SEQ ID NO: 7) (MTPLLTLILWLMGLPLAQALDCHVCAYN-GDNCFNPMRCPAMVAYCMTTRTYYTP-TRMKVSK-SCVPRCFETVYDGYSKHASTTSCCQYDLCNGTGLAT-PATLALAP ILLATLWGL L), mature lynx1 protein (SEQ ID NO: 8)(LDCHVCAYNGDNCFNPMRCPAMVAYCMT-TRTYYTPTRMKVSKSCVPRCFETVYDGYSKHASTT-SCCQYDLCN), any isoform of full length lynx2 protein including (SEQ ID NO: 9) (MQAPRAAPAA PLSYDRRL-RGSIAATFCGLF LLPGFALQIQ CYQCEEFQLN NDC-SSPEFIVNCTVNVQDMC QKEVMEQSAG IMYRK-SCASS AACLIASAGY QSFCSPGKLN SVCISCCNTPL-CNGPRPKKR GSSASALRPG LRTTILFLKLALFSAHC), and (SEQ ID NO: 10) (MCGGGRRGRQ-EGGGDVERRS QPSPPATPTPTRRPSRGAWS GRWGEKARLLWVLRI-ASSSF-SLSRQLRRRG ARPGSASGRS GDPQPGARA-RAMQAPRAAPA APLSYDRRPR DSGRMWVLGIAAT-FCGLFLL PGFALQIQCYQCEEFQLNND CSSPEFIVNC TVNVQDMCQKEVMEQSAGIMYRKSCASSAA CLIASAGYQSFCSPGKLNSV CISCCNTPLCNGPRPK-KRGSSASALRPGLPTTILLLKLALFSAHC), mature lynx1 protein (SEQ ID NO: 1), clozapine, COG133 peptide, elapid snake venom toxins, and/or marine snail toxins. The function of these selective α7 AChR antagonists is described in the art, for example, for MLA: S. Wonnacott et al., (1993), Methods in Neurosciences, Vol. 12, (P. M. Conn, Ed.), pp. 263-275, San Diego: Academic Press; for lynx1 protein: Miwa et al. 1999, *Neuron* 23, 105-114. PMCID:10402197, Ibanez-Tallon, I, Miwa, et al, (2002) *Neuron* 33, 893-903. PMID:11906696, Lyukmanova et al., (2011) JBC, 286, 10618-10627; for lynx2 protein: Tekinay, et al., (2009) A role for LYNX2 in anxiety-related behavior. Proc. Natl.

Acad. Sci. 106, 4477-4482. PMID:19246390; for condelphine: S. W. Pelletier, et al., *Acta Cryst.* (1977) B33, 716-722; for clozapine: Neuropharmacology, 2007 February; 52(2):387-94; Singhal et al., *Int J Mol Sci.* 2012; 13(2):2219-38. doi: 10.3390/ijms13022219; and for COG133 peptide: Gay et al., (2006) *J. Pharmacol. Exp. Ther.* 316 835. PMID: 16249370, the entire contents of all of which are herein incorporated by reference.

In some embodiments of the present invention, the α7AChR antagonist may include the elapid snake venom toxins (also referred to as alpha-neurotoxins) which include any of the elapid snake venom protein toxins having a "three-finger fold" or "toxin-fold" polypeptide having 4 or 5 disulfide bonds. Non-limiting examples of elapid snake venom toxins include alpha-bungarotoxin and alpha-cobratoxin. Alpha-neurotoxins are described in the art, for example, Moise, L.; et al. (2002), *Journal of Biological Chemistry,* 277 (14): 12406-12417. doi:10.1074/jbc.M110320200. PMID 11790782; Young et al., *Biophysical Journal,* 85 (2): 943-953, and Betzel et al., *Journal of Biological Chemistry,* 266 (32): 21530-6, the entire contents of all of which are herein incorporated by reference.

In some embodiments of the present invention, the α7AChR antagonist may include a marine snail toxin, for example, alpha-conotoxin, as described in Balaji et al., *J. Biol. Chem.* 275 (50): 39516-39522, the entire content of which is herein incorporated by reference.

An effective amount of the nicotinic receptor blocker and/or the α7 AChR antagonist may be administered to the subject by any suitable method. As used herein, an "effective amount" is any amount that, during the course of therapy, will have a preventive or ameliorative effect on anxiety in a subject compared to the same subject having not taken any nicotinic receptor blocker and/or α7 AChR antagonist. For example, an effective amount may be an amount that prevents the occurrence or recurrence, or reduces the frequency or degree of anxiety in a subject. In some embodiments, an effective amount of the nicotinic receptor blocker and/or α7 AChR antagonist reduces anxiety in a subject having a lynx2 mutation compared to the same subject having not been administered an effective amount of a nicotinic receptor blocker and/or α7 AChR antagonist. Quantitatively, the effective amount may vary, e.g., depending upon the subject, the severity of the disorder or symptom being treated, and the route of administration. Such and effective amount (or dose) can be determined by routine studies.

For therapeutic or prophylactic use, at least one nicotinic receptor blocker and/or α7 AChR antagonist may be administered as a pharmaceutical composition comprising the nicotinic receptor blocker and/or α7 AChR antagonist as the (or an) essential active ingredient as well as a solid or liquid pharmaceutically acceptable carrier and, optionally, one or more pharmaceutically acceptable adjuvants and excipients, employing standard and conventional techniques.

Pharmaceutical compositions useful in the practice of embodiments of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicles (including edible oils), preservatives, as well as flavoring and/or coloring agents. For parenteral administration, a vehicle normally will comprise sterile water, at least in large part, although saline solutions, glucose solutions and the like may be utilized. Injectable suspensions also may be used, in which case, conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of the nicotinic receptor blocker and/or α7 AChR antagonist. See, for example, Remington's Pharmaceutical. Sciences, Mack Publishing Company, Easton, Pa., 18th edition, 1990.

In some embodiments of the present invention, the subject being treated may have a lynx2 mutation and has anxiety and/or at least one anxiety disorder selected from the group consisting of post-traumatic stress disorder (PTSD), generalized anxiety disorder (GAD), panic-social phobia, phobia, social anxiety, depression, obsessive compulsive disorder (OCD), and agoraphobia.

In some embodiments of the present invention, a kit for identifying a subject having a lynx2 mutation or for determining the presence of a lynx2 mutation in a subject suffering from anxiety, includes at least one of two oligonucleotide primers for amplifying the lynx2 gene. In some embodiments the kit includes at least one of a forward primer (L2F): GTGGGATGGTCGTGATTTCCG (SEQ ID NO: 11) and a reverse primer L2R:GTGAGGGGGCCATTAAATAGC (SEQ ID NO: 12). In some embodiments, the kit includes both the forward and the reverse primer.

The kit, according to embodiments of the present invention, may include at least the L2F primer of SEQ ID NO: 11 to be used with an allele-specific probe for amplifying single nucleotide polymorphisms (SNPs). For example, an allele-specific probe may be readily made to amplify the Q39H SNP using the TaqMan® 5-nuclease assay from Thermo-Fisher together with the L2F primer.

In some embodiments of the present invention, the kit also includes a therapeutically effective amount of the nicotinic receptor blocker and/or α7 AChR antagonist t for treating a subject suffering from anxiety. In some embodiments, the nicotinic receptor blocker may be selected from mecamylamine, quirestine, hexamethonium bromide, tempoxime hydrochloride, buprorion, amantidine, memantine, enantiomers thereof, and combinations thereof. In some embodiments, the α7 AChR antagonist may be selected from condelphine and enantiomers thereof, methyllycaconitine (MLA) and enantiomers thereof, lynx1 protein, lynx2 protein, an elapid snake venom toxin protein, a marine snail toxin protein, COG133 peptide, and combinations thereof.

The following examples are provided for illustrative purposes only, and do not limit the scope of the embodiments of the present invention.

EXAMPLES

Materials and Methods

C57BL/6 and lynx2 KO mice fourteen to twenty-two days old of both sexes were used. Animals were housed in the Central Animal Facility at Lehigh University, under 12 hour light/12 hour dark conditions. They were housed under IACUC guidelines. It is assumed that there is no sex difference in the results.

The animals were anesthetized by isoflurane in an anesthetic chamber to a tolerant state (ml/kg) and euthanized through decapitation. The brain was removed into ice-cold (<40 C) sucrose solution containing (in mM) NaCl 87; KCl 2.5; NaH2PO4 1.25; NaHCO3 25; CaCl2 0.5; MgSO4 7.0; sucrose 75; and glucose 25. Brain tissue block was glued to stage of vibratome (Leica VT1000S). Frontal brain slices of 300 µM were cut and transferred into sucrose solution for 45 min (35.50 C). Whole cell recordings for principal neurons in BLA were conducted at ambient temperature. The extracellular solution contained (in mM) NaCl 128; KCl 2.5; NaH2PO4 1.25; CaCl2 2; MgSO4 1.0; NaHCO3 26; and dextrose 10 (pH 7.4 when bubbled with 95% 025% CO2; 300-310 milliosmolar). The resistance of the recording pipette was 4-6 MΩ. K+ based intracellular solution was used for the basic properties of principal (Table 1) K+-gluconate 120; KCl 6; ATP-Mg 4; Na2GTP 0.3; EGTA 0.1; Hepes 10 (pH 7.3); Cs+ solution for sIPSCs (and synchronization) containing 140 mM CsCl, 10 mM Hepes, 10 mM EGTA, 2 mM MgATP, 1 mM CaCl2, 5 mM lidocaine derivative QX-314 (pH 7.3 with CsOH, 295-305 milliosmolar) and Cs+ solution for sEPSCs recording containing (in mM) Cs-gluconate 120; lidocaine 5 (QX-314); CsCl2 6; ATP-Mg 1; Na2GTP 0.2; and Hepes 10 (pH 7.3, adjusted with CsOH).

TABLE 1

Showing basic properties of BLA pyramidal cell in WT and lynx2KO

|  | WT | Lynx2KO | P value |
| --- | --- | --- | --- |
| Resting membrane potential (mV) | −70.1 ± 1.64 | -65.6 ± 1.64 | 0.084 |
| Input resistance (MΩ) | 146 ± 8.44 | 170 ± 12.8 | 0.129 |
| Membrane time constant (ms) | 12.5 ± 1.56 | 11.1 ± 2.61 | 0.622 |
| AP threshold (mV) | −42.5 ± 1.03 | −42.3 ± 0.93 | 0.896 |
| AP half-width (ms) | 1.74 ± 0.05 | 2.01 ± 0.16 | 0.071 |
| After hyperpolarization (mV) | −5.82 ± 0.79 | −7.55 ± 1.45 | 0.267 |

Spontaneous inhibitory postsynaptic currents (sIPSCs) were recorded for 10 minutes at a holding potential of −70 mV in the bath with ACSF in the presence of 2,3-dihydroxy-6-nitro-7-sulfamoyl-benzo[f]quinoxaline-2,3-dione (NBQX; 20 µM, Tocris) and D-2-amino-5-phosphonovalerate (DAP-5; 50 µM, Tocris) to block glutamatergic transmissions. Spontaneous excitatory postsynaptic currents (sEPSCs) were recorded in same way, but in the presence of picrotoxin (PTX; 50 µM, Sigma-Aldrich, St. Louis, Mo.) to block GABAergic transmissions. Nicotine was dissolved in ACSF for the bath of recording neuron. To examine the synchronization of IPSC, double electrodes recording was carried out.

Field excitatory postsynaptic potentials (fEPSPs) were evoked by 0.05 Hz test stimulus though a bipolar stimulating electrode placed on external Capsule (EC), and a glass pipette as recording electrode was filled with ACSF and placed in BLA. For LTP induction, high-frequency stimulation (HFS) of 100 Hz with the 1-s duration was applied four times with a 10-s interval, whereas LTD induction utilized natural theta pulse stimulations (TPS 5 Hz for 180 s); test stimulation was continued for the indicated periods. The signals were acquired with pCLAMP 10.3 (Molecular Devices). Access resistances were continuously monitored and neurons with more than 20% change of series resistance were excluded from data analysis.

Graded series of hyperpolarizing and depolarizing current pulses in 50 pA increments (1.5-s duration) from −100 pA to +100 pA were injected to measure the electroresponsive properties of principal cells in BLA. The input resistance (Rin) of the cells was estimated in the linear portion of current-voltage plots. The amplitude of the slow afterhyperpolarizations (AHPs) was measured at its peak after the offset of the current pulse. sIPSCs and sEPSCs recorded in the voltage-clamp mode were analyzed with Clampfit 10.3. The typical events in separate relevant experiments were selected to create sample templates for event detection within a data period, and sIPSCs and sEPSCs were detected with a threshold set at three times the value of the root mean square of the baseline noise. The event distribution was sorted and histogrammed at a bin size of 1 pA. The histogram could be fitted with a Gaussian function. The coefficient of variation (CV) of synaptic currents can be used to identify the changes of quantal release and pre- or postsynaptic effects. The ratio of mean amplitude (M) of treatment in each cell was first normalized to that of control and then plotted against the ratio of CV2 in each condition, respectively.

The plasticity ratio was calculated from the average EPSP amplitude of the last 10 mins of baseline recording and the last 15 mins after high frequency or low stimulus, for LTP and LTD studies, respectively. Data is represented as an absolute change from the baseline plasticity. For all experiments, treatment effects were analyzed with one-way ANOVA, followed by the appropriate post hoc tests. Paired Student's t test was used when comparisons were restricted to two means in the neuronal samples (e.g., baseline and nicotine application). The Kolmogorov-Smirnov (K-S) analysis was applied to analyze the amplitude and inter-event interval of sIPSCs and sEPSCs. Error probability of p<0.05 was considered to be statistically significant and the data were presented as mean±standard error.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of treating anxiety in a subject having anxiety and a single lynx2 mutation, the single lynx2 mutation comprising a substitution or deletion of glutamine (Q) at amino acid position 39 of a mature lynx2 protein, the method comprising:

administering to the subject having anxiety and the single lynx2 mutation:

an effective amount of a nicotinic blocker selected from the group consisting of mecamylamine, quirestine, hexamethonium bromide, tempoxime hydrochloride, buproprion, amantidine, memantine, enantiomers thereof, and combinations thereof;

and/or an effective amount of a selective antagonist of a nicotinic acetylcholine receptor alpha-7 (nAChR α7) subunit selected from the group consisting of methyllycaconitine, condelphine, aconitane, talatisamine, bullatine B, delphamine, bikhaconitine, pyrodelphonine, winklerlin, delelatine, lynx1 protein, lynx2 protein, an elapid snake venom toxin protein, a marine snail toxin protein, clozapine, COG133 peptide, and combinations thereof.

2. The method of claim 1, wherein the single lynx2 mutation comprises the substitution of glutamine (Q) with histidine (H) at amino acid position 39 of the mature lynx2 protein.

3. The method of claim 1, wherein the elapid snake venom toxin protein is alpha-bungarotoxin or alpha-cobratoxin.

4. The method of claim 1, wherein the marine snail toxin protein is alpha-conotoxin.

5. The method of claim 1, wherein the subject having anxiety has at least one anxiety disorder selected from the group consisting of post-traumatic stress disorder (PTSD), generalized anxiety disorder (GAD), panic-social phobia, phobia, social anxiety, depression, obsessive compulsive disorder (OCD), and agoraphobia.

6. The method of claim 1, wherein the nicotinic blocker is mecamylamine, the selective antagonist of the nAChR α7 subunit is methyllycaconitine (MLA) and the method comprises administering to the subject the mecamylamine, MLA, or a combination thereof.

\* \* \* \* \*

SEQUENCE LISTING

<160> NUMBER OF SEQ ID NOS: 12

<210> SEQ ID NO 1
<211> LENGTH: 85
<212> TYPE: PRT
<213> ORGANISM: Homo sapiens

<400> SEQUENCE: 1

-continued

Ile Gln Cys Tyr Gln Cys Glu Glu Phe Gln Leu Asn Asn Asp Cys Ser
1               5                   10                  15

Ser Pro Glu Phe Ile Val Asn Cys Thr Val Asn Val Gln Asp Met Cys
            20                  25                  30

Gln Lys Glu Val Met Glu Gln Ser Ala Gly Ile Met Tyr Arg Lys Ser
        35                  40                  45

Cys Ala Ser Ser Ala Ala Cys Leu Ile Ala Ser Ala Gly Tyr Gln Ser
    50                  55                  60

Phe Cys Ser Pro Gly Lys Leu Asn Ser Val Cys Ile Ser Cys Cys Asn
65                  70                  75                  80

Thr Pro Leu Cys Asn
            85

<210> SEQ ID NO 2
<211> LENGTH: 104
<212> TYPE: PRT
<213> ORGANISM: Homo sapiens

<400> SEQUENCE: 2

Val Gly Pro Arg His Arg Gly Asn Phe Leu Arg Ile Val Leu Ala Ser
1               5                   10                  15

Arg Leu Cys Ala Ala Asn Pro Val Leu Pro Val Arg Ile Pro Ala Glu
            20                  25                  30

Gln Arg Leu Leu Leu Pro Arg Val His Cys Glu Leu His Gly Glu Arg
        35                  40                  45

Ser Arg His Val Ser Glu Arg Ser Asp Gly Ala Lys Cys Arg Asp His
    50                  55                  60

Val Pro Gln Val Leu Cys Ile Ile Ser Gly Leu Ser His Arg Leu Cys
65                  70                  75                  80

Arg Val Pro Val Leu Leu Leu Pro Arg Glu Thr Glu Leu Ser Leu His
                85                  90                  95

Gln Leu Leu Gln His Pro Ser Leu
            100

<210> SEQ ID NO 3
<211> LENGTH: 83
<212> TYPE: PRT
<213> ORGANISM: Homo sapiens

<400> SEQUENCE: 3

Ile Gln Cys Tyr Gln Cys Glu Glu Phe Gln Leu Asn Asn Asp Cys Ser
1               5                   10                  15

Ser Pro Glu Phe Ile Val Asn Cys Thr Val Asn Val Gln Asp Met Cys
            20                  25                  30

Gln Lys Glu Val Met Glu Gln Ser Ala Gly Ile Met Tyr Arg Ile Leu
        35                  40                  45

Cys Ile Ile Ser Gly Leu Ser His Arg Leu Cys Arg Val Pro Val Leu
    50                  55                  60

Leu Leu Pro Arg Glu Thr Glu Leu Ser Leu His Gln Leu Leu Gln His
65                  70                  75                  80

Pro Ser Leu

<210> SEQ ID NO 4
<211> LENGTH: 83
<212> TYPE: PRT
<213> ORGANISM: Homo sapiens

<400> SEQUENCE: 4

Ile Gln Cys Tyr Gln Cys Glu Glu Phe Gln Leu Asn Asn Asp Cys Ser
1               5                   10                  15

Ser Pro Glu Phe Ile Val Asn Cys Thr Val Asn Val Gln Asp Val Ser
                20                  25                  30

Glu Arg Ser Asp Gly Ala Lys Cys Arg Asp His Val Pro Gln Val Leu
            35                  40                  45

Cys Ile Ile Ser Gly Leu Ser His Arg Leu Cys Arg Val Pro Val Leu
50                  55                  60

Leu Leu Pro Arg Glu Thr Glu Leu Ser Leu His Gln Leu Leu Gln His
65                  70                  75                  80

Pro Ser Leu

<210> SEQ ID NO 5
<211> LENGTH: 22
<212> TYPE: PRT
<213> ORGANISM: Homo sapiens

<400> SEQUENCE: 5

Ile Gln Cys Tyr Gln Cys Glu Glu Phe Gln Leu Asn Asn Asp Cys Ser
1               5                   10                  15

Ser Pro Glu Phe Ile Gln
            20

<210> SEQ ID NO 6
<211> LENGTH: 28
<212> TYPE: PRT
<213> ORGANISM: Homo sapiens

<400> SEQUENCE: 6

Ile Gln Cys Tyr Gln Cys Glu Glu Phe Gln Leu Asn Asn Asp Cys Ser
1               5                   10                  15

Ser Pro Glu Phe Ile Val Asn Cys Thr Val Asn Val
            20                  25

<210> SEQ ID NO 7
<211> LENGTH: 116
<212> TYPE: PRT
<213> ORGANISM: Homo sapiens

<400> SEQUENCE: 7

Met Thr Pro Leu Leu Thr Leu Ile Leu Val Leu Met Gly Leu Pro
1               5                   10                  15

Leu Ala Gln Ala Leu Asp Cys His Val Cys Ala Tyr Asn Gly Asp Asn
                20                  25                  30

Cys Phe Asn Pro Met Arg Cys Pro Ala Met Val Ala Tyr Cys Met Thr
            35                  40                  45

Thr Arg Thr Tyr Tyr Thr Pro Thr Arg Met Lys Val Ser Lys Ser Cys
50                  55                  60

Val Pro Arg Cys Phe Glu Thr Val Tyr Asp Gly Tyr Ser Lys His Ala
65                  70                  75                  80

Ser Thr Thr Ser Cys Cys Gln Tyr Asp Leu Cys Asn Gly Thr Gly Leu
                85                  90                  95

Ala Thr Pro Ala Thr Leu Ala Leu Ala Pro Ile Leu Leu Ala Thr Leu
            100                 105                 110

Trp Gly Leu Leu
        115

```
<210> SEQ ID NO 8
<211> LENGTH: 72
<212> TYPE: PRT
<213> ORGANISM: Homo sapiens

<400> SEQUENCE: 8

Leu Asp Cys His Val Cys Ala Tyr Asn Gly Asp Asn Cys Phe Asn Pro
1               5                   10                  15

Met Arg Cys Pro Ala Met Val Ala Tyr Cys Met Thr Thr Arg Thr Tyr
            20                  25                  30

Tyr Thr Pro Thr Arg Met Lys Val Ser Lys Ser Cys Val Pro Arg Cys
        35                  40                  45

Phe Glu Thr Val Tyr Asp Gly Tyr Ser Lys His Ala Ser Thr Thr Ser
    50                  55                  60

Cys Cys Gln Tyr Asp Leu Cys Asn
65                  70

<210> SEQ ID NO 9
<211> LENGTH: 157
<212> TYPE: PRT
<213> ORGANISM: Homo sapiens

<400> SEQUENCE: 9

Met Gln Ala Pro Arg Ala Ala Pro Ala Ala Pro Leu Ser Tyr Asp Arg
1               5                   10                  15

Arg Leu Arg Gly Ser Ile Ala Ala Thr Phe Cys Gly Leu Phe Leu Leu
            20                  25                  30

Pro Gly Phe Ala Leu Gln Ile Gln Cys Tyr Gln Cys Glu Glu Phe Gln
        35                  40                  45

Leu Asn Asn Asp Cys Ser Ser Pro Glu Phe Ile Val Asn Cys Thr Val
    50                  55                  60

Asn Val Gln Asp Met Cys Gln Lys Glu Val Met Glu Gln Ser Ala Gly
65                  70                  75                  80

Ile Met Tyr Arg Lys Ser Cys Ala Ser Ser Ala Ala Cys Leu Ile Ala
                85                  90                  95

Ser Ala Gly Tyr Gln Ser Phe Cys Ser Pro Gly Lys Leu Asn Ser Val
            100                 105                 110

Cys Ile Ser Cys Cys Asn Thr Pro Leu Cys Asn Gly Pro Arg Pro Lys
        115                 120                 125

Lys Arg Gly Ser Ser Ala Ser Ala Leu Arg Pro Gly Leu Arg Thr Thr
    130                 135                 140

Ile Leu Phe Leu Lys Leu Ala Leu Phe Ser Ala His Cys
145                 150                 155

<210> SEQ ID NO 10
<211> LENGTH: 255
<212> TYPE: PRT
<213> ORGANISM: Homo sapiens

<400> SEQUENCE: 10

Met Cys Gly Gly Gly Arg Arg Gly Arg Gln Glu Gly Gly Gly Asp Val
1               5                   10                  15

Glu Arg Arg Ser Gln Pro Ser Pro Ala Thr Pro Thr Pro Thr Arg
            20                  25                  30

Arg Pro Ser Arg Gly Ala Trp Ser Gly Arg Trp Gly Glu Lys Ala Arg
        35                  40                  45

Leu Leu Trp Val Leu Arg Ile Ala Ser Ser Ser Phe Ser Leu Ser Arg
    50                  55                  60
```

```
Gln Leu Arg Arg Arg Gly Ala Arg Pro Gly Ser Ala Ser Gly Arg Ser
 65                  70                  75                  80

Gly Asp Pro Gln Pro Gly Ala Arg Ala Arg Ala Met Gln Ala Pro Arg
                 85                  90                  95

Ala Ala Pro Ala Ala Pro Leu Ser Tyr Asp Arg Arg Pro Arg Asp Ser
                100                 105                 110

Gly Arg Met Trp Val Leu Gly Ile Ala Ala Thr Phe Cys Gly Leu Phe
            115                 120                 125

Leu Leu Pro Gly Phe Ala Leu Gln Ile Gln Cys Tyr Gln Cys Glu Glu
130                 135                 140

Phe Gln Leu Asn Asn Asp Cys Ser Ser Pro Glu Phe Ile Val Asn Cys
145                 150                 155                 160

Thr Val Asn Val Gln Asp Met Cys Gln Lys Glu Val Met Glu Gln Ser
                165                 170                 175

Ala Gly Ile Met Tyr Arg Lys Ser Cys Ala Ser Ser Ala Ala Cys Leu
            180                 185                 190

Ile Ala Ser Ala Gly Tyr Gln Ser Phe Cys Ser Pro Gly Lys Leu Asn
            195                 200                 205

Ser Val Cys Ile Ser Cys Cys Asn Thr Pro Leu Cys Asn Gly Pro Arg
210                 215                 220

Pro Lys Lys Arg Gly Ser Ser Ala Ser Ala Leu Arg Pro Gly Leu Pro
225                 230                 235                 240

Thr Thr Ile Leu Leu Leu Lys Leu Ala Leu Phe Ser Ala His Cys
                245                 250                 255

<210> SEQ ID NO 11
<211> LENGTH: 21
<212> TYPE: DNA
<213> ORGANISM: Artificial Sequence
<220> FEATURE:
<223> OTHER INFORMATION: Lynx2 forward primer (L2F)

<400> SEQUENCE: 11
gtgggatggt cgtgatttcc g                                         21

<210> SEQ ID NO 12
<211> LENGTH: 21
<212> TYPE: DNA
<213> ORGANISM: Artificial Sequence
<220> FEATURE:
<223> OTHER INFORMATION: Lynx2 reverse primer (L2R)

<400> SEQUENCE: 12 gtgaggggc cattaaatag c                                          21
```